United States Patent [19]

Turkel et al.

[11] Patent Number: 5,524,634
[45] Date of Patent: Jun. 11, 1996

[54] METHODS AND APPARATUS FOR RECORDING THE SOURCE AND ORIENTATION OF AS WELL AS FOR STORING AND IDENTIFYING MULTIPLE BIOPSY SAMPLES

[75] Inventors: David Turkel; Sarah E. Gillim, both of Miami, Fla.

[73] Assignee: Symbiois Corporation, Miami, Fla.

[21] Appl. No.: 277,255

[22] Filed: Jul. 19, 1994

[51] Int. Cl.⁶ ................................................. A61B 10/00
[52] U.S. Cl. .............................................................. 128/749
[58] Field of Search ................................. 128/749, 752, 128/753, 758, 760, 762, 759; 604/317–319, 403, 404, 189; 206/363, 570, 571; 283/81

[56] References Cited

U.S. PATENT DOCUMENTS

| | | | |
|---|---|---|---|
| 3,863,624 | 2/1975 | Gram | 128/758 |
| 4,042,337 | 8/1977 | Griffith | 128/762 |
| 5,084,041 | 1/1992 | Oxley et al. | 604/317 |
| 5,119,830 | 6/1992 | Davis | 604/404 |
| 5,352,155 | 10/1994 | Fahey | 283/81 |

FOREIGN PATENT DOCUMENTS

| | | | |
|---|---|---|---|
| 0510615 | 10/1992 | European Pat. Off. | 128/760 |

OTHER PUBLICATIONS

Burke, Louis, et al., Colposcopy Text and Atlas, 1991, p. 27.

*Primary Examiner*—Max Hindenburg
*Attorney, Agent, or Firm*—David P. Gordon

[57] ABSTRACT

Apparatus and methods are disclosed for recording the source and orientation of biopsy samples typically taken with a multiple biopsy sample instrument. The apparatus includes a multiple compartment fixative cup and a multiple copy record keeping label form. The fixative cup is preferably cylindrical and has several compartments defined by sector walls as well as by concentric cylindrical walls. The multiple copy record keeping label form preferably includes a circular label with indicia corresponding to the sector walls of the fixative cup and at least one carbon or carbonless copy form. The preferred method of the invention includes the steps of obtaining biopsy samples and marking the corresponding location on the label form with an indication of order. After the several biopsy samples have been taken, and their locations marked on the label form, the biopsy samples are removed from the body and placed in order in the appropriate compartments in the fixative cup. The cup is then covered and the label is removed from the label form and applied to the fixative cup. The carbon or carbonless copy of the label is placed in the chart or file of the patient.

23 Claims, 6 Drawing Sheets

METHODS AND APPARATUS FOR RECORDING THE SOURCE AND ORIENTATION OF AS WELL AS FOR STORING AND IDENTIFYING MULTIPLE BIOPSY SAMPLES

This application is related to co-assigned Ser. No. 08/189,937 filed Feb. 1, 1994 which is hereby incorporated herein in its entirety.

BACKGROUND OF THE INVENTION

1. Field of the Invention

The present invention broadly relates to the storage and identification of biopsy samples. More particularly, the invention relates to methods and apparatus for storing and identifying multiple biopsy samples wherein the sources of the samples are accurately recorded. The invention has particular utility in the collection of cervical biopsy samples, although it is not limited thereto.

2. State of the Art

Biopsy is a common procedure in modern medical practice. A biopsy is the removal and examination, usually microscopic, of tissue (a biopsy sample) from the living body in order to establish a diagnosis. Biopsy samples may be taken in several ways, for example by suction, scraping, coring, puncture, etc. In all cases, however, the samples must be stored in a container with a fixative and an accurate record made of the source of the sample. The samples may then be sent to a pathologist for examination. Since the pathologist deals with many biopsy samples, accurate documentation regarding the source of each sample must be maintained at all times.

In many cases it is necessary or desirable to take several biopsy samples from specific locations in a single organ. This is particularly so in the case of cervical biopsies where samples are typically taken at several sites on the cervix. This is most often accomplished through a procedure of moving a biopsy forceps instrument to a desired location, noting the location, obtaining the biopsy, withdrawing the instrument from the biopsy site, and placing the individual biopsy sample in a fixative vial which is labeled and closed. This procedure is repeated several times until sufficient biopsies are obtained. In the cervical biopsy procedure, the practitioner must take extreme care to make and preserve accurate records (e.g., by manual notation of data on charts and paperwork accompanying each sample) regarding the source and orientation (e.g., clock orientation) of each sample in relation to the location on the cervix (e.g., internal os, central, and peripheral to os locations) where the sample was taken. This is because the pathologist makes a diagnosis by examining the several samples in consideration of their specific locations on the cervix. In addition, the separate vials must be kept together and a copy of the sample records placed in the file of the patient. During the course of this procedure, it is always possible that a vial will be mislabeled or lost and that a record will be inaccurate or lost.

It should be appreciated that the entire biopsy procedure is a rather lengthy and tedious one due to the lengthy procedure required for each biopsy sample, and due to the necessity of obtaining several individual biopsies and placing them in individual containers. As disclosed in related U.S. Ser. No. 08/189,937, instruments are becoming available which can obtain several biopsy samples without the necessity of removing each biopsy sample from the instrument prior to obtaining additional biopsies. However, while such an instrument will decrease the length of the procedure, the procedure still necessitates the use of numerous vials which must be separately labeled and kept together. Furthermore, subsequent retrieval of the biopsy samples from the vials for diagnosis by a pathologist is a messy and potentially time consuming procedure.

SUMMARY OF THE INVENTION

It is therefore an object of the invention to provide methods and apparatus for use in multiple sample biopsy procedures which simplify record keeping.

It is also an object of the invention to provide methods and apparatus for use in multiple sample biopsy procedures which reduce errors in record keeping.

It is another object of the invention to provide methods and apparatus for use in multiple sample biopsy procedures which reduce the possibility of losing or misplacing a sample.

It is still another object of the invention to provide methods and apparatus for use in multiple sample biopsy procedures which provide accurate duplicate records of the samples taken.

It is also an object of the invention to provide methods and apparatus for use in multiple sample biopsy procedures which reduce the number of fixative vials required.

It is yet another object of the invention to provide methods and apparatus for use in multiple sample biopsy procedures which facilitate the retrieval and diagnosis of stored biopsy samples.

In accord with these objects which will be discussed in detail below, the apparatus of the present invention includes a multiple compartment fixative cup and a multiple copy record keeping label form. The fixative cup is preferably cylindrical and has several compartments defined by sector walls. The multiple copy record keeping label form preferably includes a circular label with indicia corresponding to the sector walls of the fixative cup and at least one carbon or carbonless copy form. The method of the invention includes the steps of obtaining biopsy samples and marking the corresponding location on the label form. After the several biopsy samples have been taken, and their locations marked on the label form (with order noted), the biopsy samples are removed from the body and placed in the appropriate compartments in the fixative cup. The cup is then covered and the label is removed from the label form and applied to the fixative cup. The carbon or carbonless copy of the label is placed in the chart or file of the patient. An alternative method of the invention includes the steps of obtaining a biopsy sample, removing it from the body and placing it in the container, and marking the corresponding location on the label form. These steps are repeated until the cup is full or the biopsy procedure is completed.

Preferred aspects of the invention include further dividing the fixative cup into annular zones defined by concentric cylindrical walls and identifying each compartment with coordinates. In this configuration, the compartments of the fixative cup are correlated to locations on the cervix for the collection of multiple cervical biopsy samples. The preferred label form also includes indicia relating to the sectors and zones defining the compartments and may also include the coordinates of each compartment relating it to a location on the cervix. The label form may also include additional indicia, reference material, instructions and the like printed on it to aid in performing the method of the invention. As yet an additional embodiment of the invention, the biopsy sample compartments of the invention may be in a seperate perforated biopsy sample holder with a handle and perforated bottom as opposed to the container. The biopsy sample holder has an open top, perforated bottom and has a height and diameter slightly less than that of the container, such that it may be inserted and removed from the container by means of the handle. Initially, the biopsy samples are stored within the multiple fixative filled compartments of the biopsy sample holder according to the method of the invention. The biopsy samples may be subsequently retrieved by removing the biopsy sample holder from the container and allowing the fixative to drain into the container via the perforated bottom of the biopsy sample holder. The biopsy samples may then be manually retrieved without the encumbrance of excess fixative.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
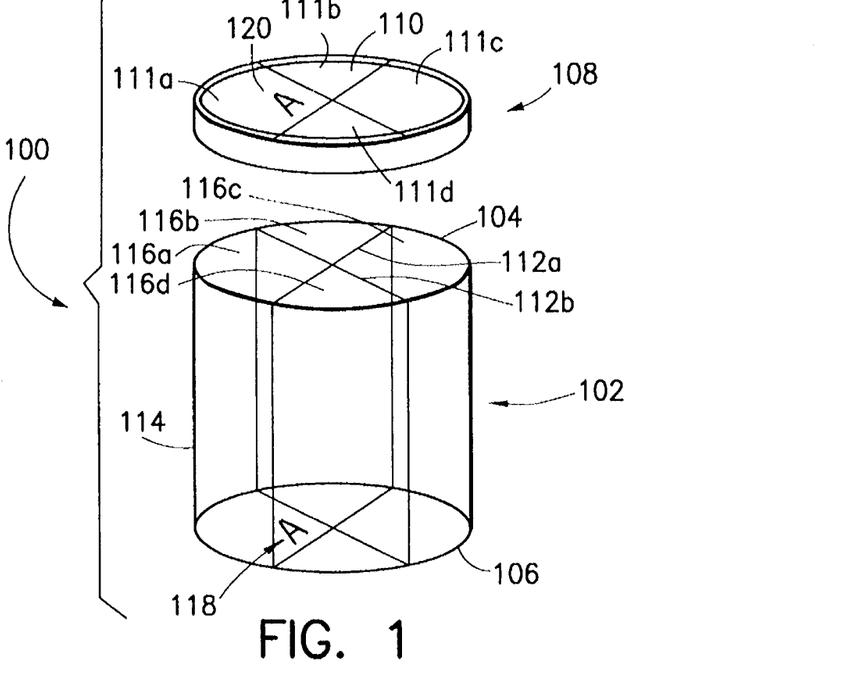
FIG. 1 is a perspective view of a first embodiment of a multiple sample fixative cup according to the invention.

Turning now to FIG. 1, a first embodiment of the invention includes a multiple compartment fixative cup 100 having a cylindrical container 102 with an open top end 104 and a closed bottom end 106 and a removable cap or cover 108. A pair of diametrical sector walls 112a and 112b, preferably of similar height to the container 102 intersect the cylindrical container wall 114 and the container bottom 106 to form four compartments 116a–116d which are of similar shape and size. The container bottom 106 preferably includes an alignment index 118, such as a letter, an arrow, or other indication. In addition, the cover 108 may be provided with an alignment index and the container and cover may be constructed so that the the alignment indices always aligh when the cover is secured to the container.

Figure 2:
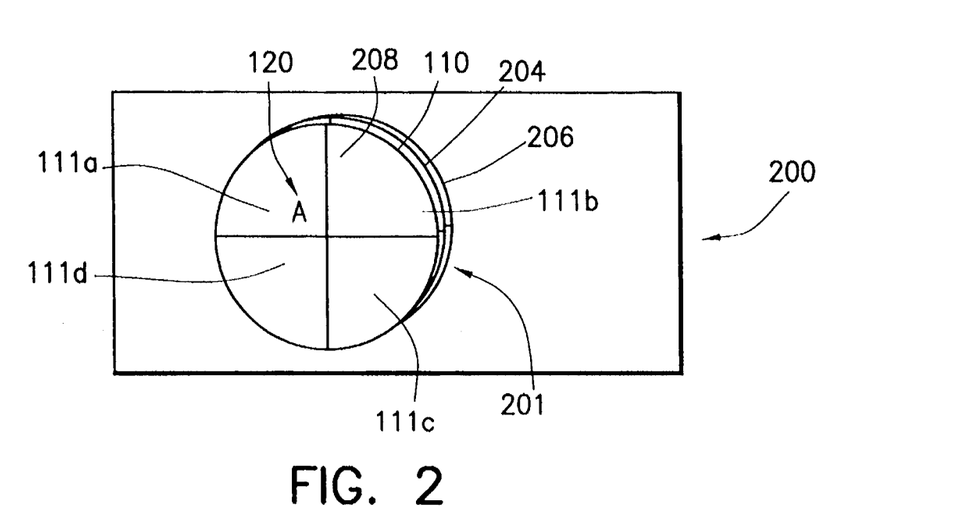
FIG. 2 is a plan view of a first embodiment of a multiple copy label form according to the invention.

Referring to FIG. 2, a first embodiment of the multiple copy record keeping label form 200 is seen. The label form 200 is preferably a multilayered sheet which contains perforations (not shown) which define one or more layered circular labeling sets 201. Each circular labeling set preferably includes the detachable circular label 110 with indicia defining four areas 111a–111d and an alignment index 120, a detachable circular first record copy 204 and a detachable circular second record copy 206. Both the first record copy 204 and the second record copy 206 preferably include the same indicia defined areas 111a–111d as the label 110. Preferably both the first and second record copies 204 and 206 are made of a carbon or pressure-sensitive material and are stacked beneath the label 110 such that upon writing on an area of the label 110, copies of the writing are made on both the first and second record copies in the same areas. The backside 208 of the top label 110 includes an adhesive (not shown) for affixing the label 110 to the removable cover 108. The label adhesive is of a type that can easily be removed from the first record copy 204 without damaging it. If desired, a layer of adhesive may be provided on the backsides of both the first and second record copies 204 and 206 as well. The alignment index 120 on the label is used for aligning the label with the container index 118 such that the label areas 111a–111d of the record keeping label 110 are properly matched with their corresponding compartments 116a–116d as shown in FIG. 1.

Figure 3:
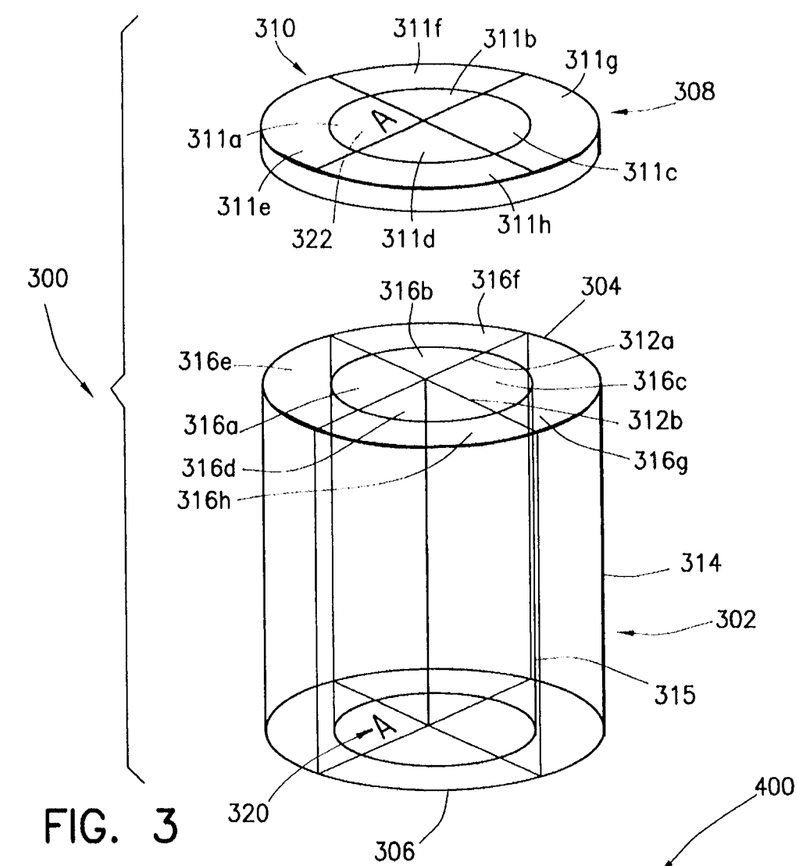
FIG. 3 is a view similar to FIG. 1, but of a second embodiment of a multiple sample fixative cup according to the invention.

Turning to FIG. 3, a second embodiment of the invention is illustrated. As in FIG. 1, a multiple compartment fixative cup 300 includes a cylindrical container 302, with an open top 304 and a closed bottom 306, a removable cover 308 and a pair of diametrical sector walls 312a and 312b. However, in the embodiment of FIG. 3, a cylindrical wall 315 of smaller radius but of substantially equal height to the container wall 314 is concentrically positioned within the container 302 and intersects the sector walls 312a and 312b, thereby forming eight "polar" compartments 316a–316h; four radially inner polar compartments, and four radially outer polar compartments. Preferably, cylindrical wall 315 is located such that the radius of the wall 315 is more than one-half the radius of the container wall 314, but that the area (volume) contained in each of the outer areas or polar compartments 316e–316h is still greater than the area (volume) contained in each of the inner areas or polar compartments 316a–316d. Such an arrangement permits biopsy samples to be easily accessed in both the inner and outer areas without sacrificing either the area of the inner areas, or the width of the outer areas. It will be appreciated that in the embodiment of FIG. 3 an aligning index 320 is provided on the container bottom 306 for aligning with an index 322 of the label so that the label areas 311a–311h can be properly matched with the corresponding container compartments 316a–316h.

Figure 4:
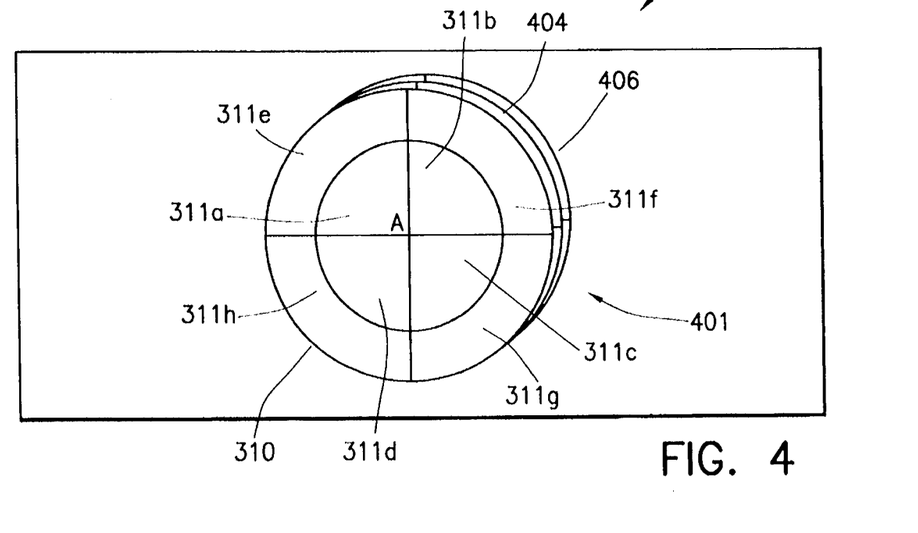
FIG. 4 is a view similar to FIG. 2, but of a second embodiment of a multiple copy label form according to the invention.

FIG. 4 shows a second embodiment of the multiple copy record keeping label form 400. Label form 400 is substantially identical to label form 200 in that it includes a layered circular labeling set 401 including label 310, and layers 404 and 406. However, the layered circular labeling set 401 is provided with indicia defining eight areas 311a–311h instead of the four areas indicated on label 110. An alignment index 322 is provided for the same reasons as described above.

Figure 5:
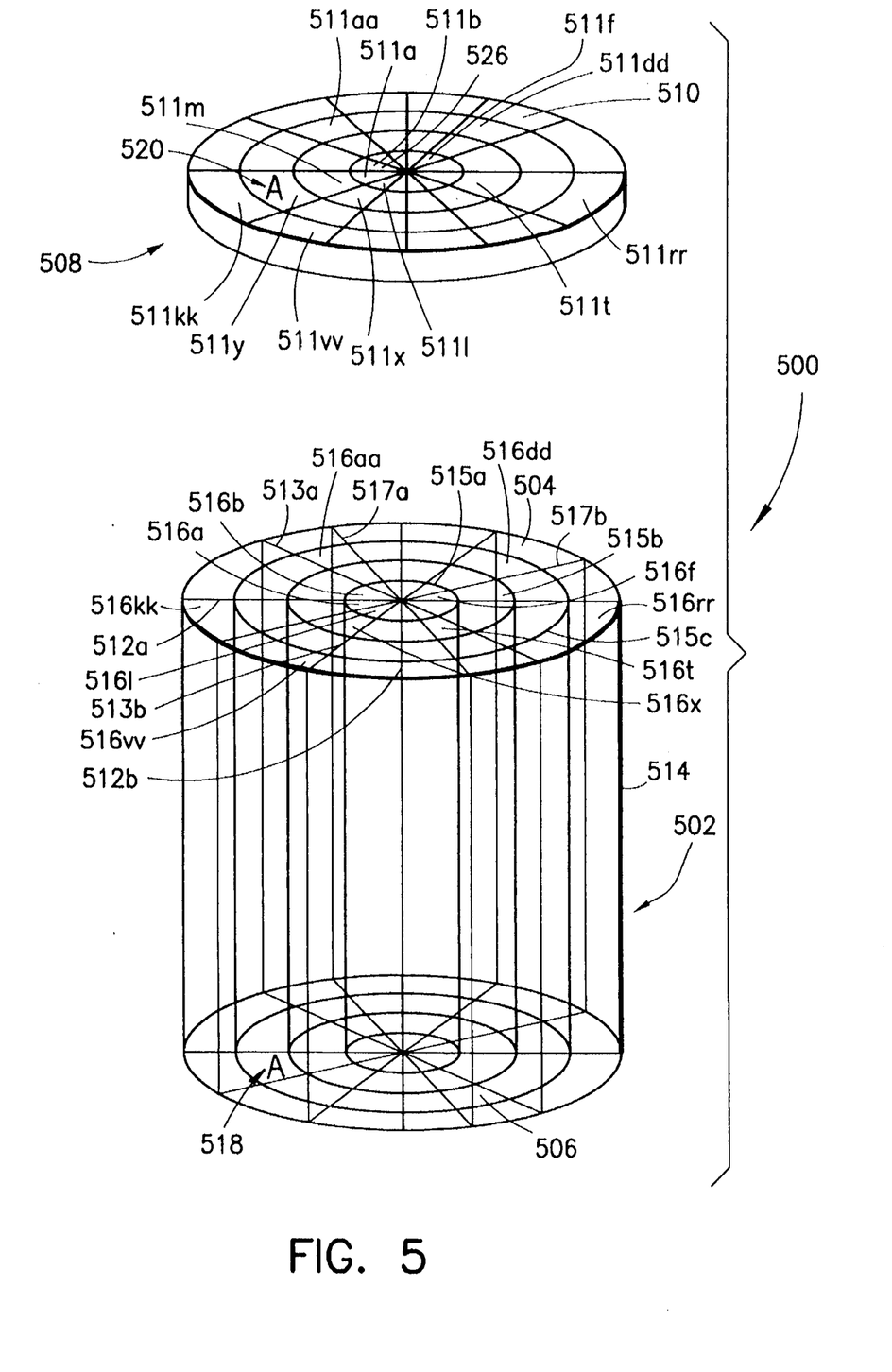
FIG. 5 is a view similar to FIG. 3, but of a third embodiment of a multiple sample fixative cup according to the invention.

A third embodiment of the invention is illustrated in FIG. 5. As in FIG. 3, a multiple compartment fixative cup 500 includes a cylindrical container 502 with an open top 504, a closed bottom 506, and an aligning index 518 on the bottom 506, and a removable cover 508. In the embodiment of FIG. 5, however, there are three pairs of diametrical sector walls 512a, 512b, 513a, 513b, and 517a, 517b, and three cylindrical walls 515a, 515b, 515c concentrically positioned within the container 502 which all intersect with each other and the container wall 514 to form forty-eight areas 516a–516vv. Preferably, the second pair of diametrical sector walls 513a and 513b are arranged at a thirty degree angle relative to the first pair of sector walls 512a and 512b and the third pair of sector walls 517a and 517b are similarly arranged at a thirty degree angle relative to the second pair of sector walls 513a and 513b. In this manner, twelve compartments are defined corresponding to twelve hourly clock locations. Furthermore, the cylindrical walls 515a, 515b, and 515c are preferably of increasing radius and concentrically positioned within the container 502 such that the formed areas 516a–516vv are of appropriate size and shape to permit the biopsy samples to be easily accessed in all of the inner areas 516a–l, the middle areas 516m–x, 516y–jj, and outer areas 516kk–vv without compromising either the areas of the inner areas, or the width of the outer areas. With the three cylindrical walls 515a, 515b, and 515c, each sector is provided with an inner, an outer, and two middle areas which will be particularly helpful in identifying cervical locations.

Figure 6:
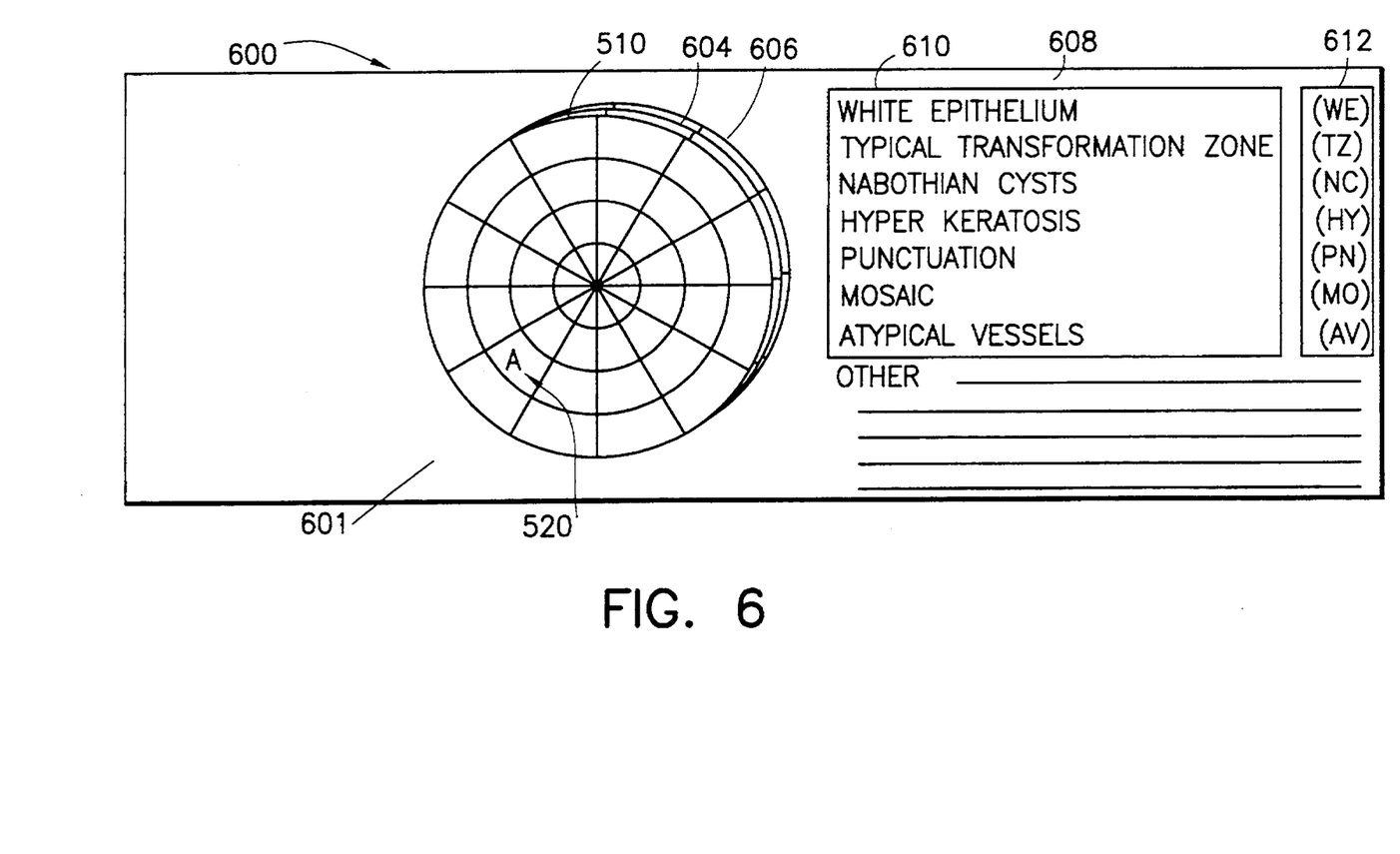
FIG. 6 is a view similar to FIG. 4, but of a third embodiment of a multiple copy label form according to the invention.

Turning to FIG. 6, a third embodiment of the multiple copy record keeping label form 600 is shown. Label form 600 is substantially identical to label form 200 in that it includes a layered circular labeling set 601 including an adhesive-backed label 510, and layers 604 and 606. However, the layered circular labeling set 601 is provided with indicia defining forty-eight areas 511a–511vv instead of the four areas provided on label 110 and the label form further includes category indicia 608. The category indicia 608 provides a list of medical diagnostic terms 610 and abbreviations 612 describing various conditions that may exist in the human cervix. It will be appreciated by those skilled in the art that any other indicia may be similarly used in the above label form. According to the method of the invention as described in more detail below, the position of each biopsy sample taken from a patient's cervix is located on the appropriate area 511a–511vv of the label 510, and the appropriate medical diagnostic term 610 or its abbreviation 612 may be recorded in the appropriate location.

Although in the above three embodiments of the invention a container index and a label index were shown for properly aligning the label areas with the corresponding compartments, another suitable configuration would include having a guiding means on the open end of the container and the the cover so that the cover can only be fitted on the container in one position. Thus, once the label is properly affixed to the cover and the cover used to close the container, the areas of the label would automatically be properly aligned with their corresponding compartments.

Figure 7:
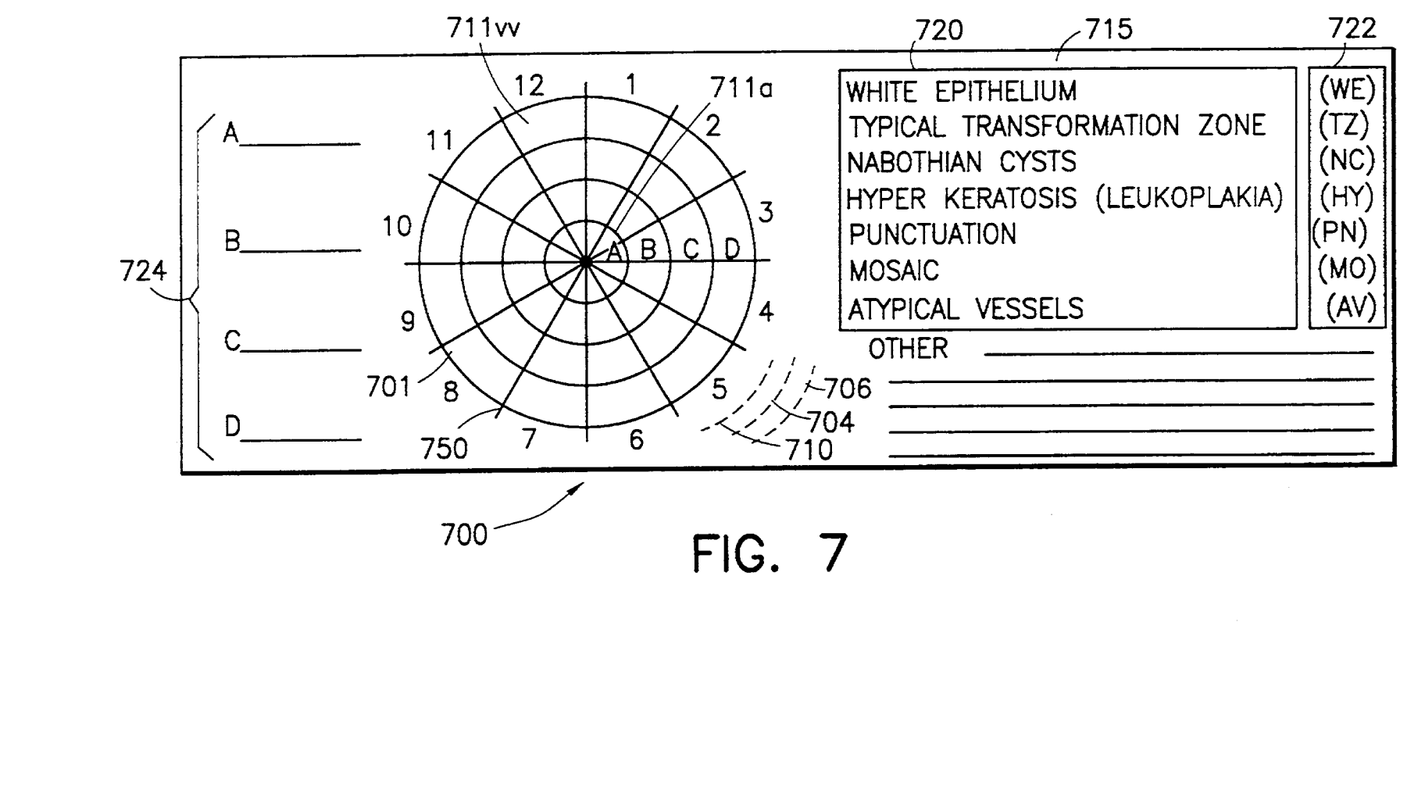
FIG. 7 is a view similar to FIG. 4, but of a fourth embodiment of a multiple copy label form according to the invention.

As seen in FIG. 7, the label form of the invention can take yet other formats. In particular, the label form 700 of FIG. 7 includes the layered circular labeling set 701 which incorporates an adhesive-backed label 710, and layers 704 and 706. The layered circular labeling set 701 is provided with indicia defining fortyeight areas 711a–711vv. The labeling set 701 includes a portion having category indicia 715 with a list of medical diagnostic terms 720 and abbreviations 722 describing various conditions that may exist in the human cervix. In addition, the labeling set 701 includes another portion 724 having polar coordinate markings (A, B, C, D) which correspond to different polar zones. Room is left for the surgeon or nurse to enter the sector number(s) corresponding to the cervix location(s) from which the biopsy or biopsies were taken and into which the biopsy or biopsies are to be placed into the multiple compartment cup of FIG. 5. Thus, upon taking a sample, the surgeon might say that the sample is being taken at the periphery of the cervix (zone D) at 2 o'clock, and that the sample appears to be a nabothian cyst. Based on that information, in portion 724 of the label next to D, the nurse might write the numeral "2" and might further mark the initials NC in the polar area D2 of areas 711a–711vv of the label. Then, the surgeon might say that another sample is being taken in the next zone in at 5 o'clock and appears to be an atypical vessel. Based on the new information, the nurse might write the numeral "5" next to the marking C on portion 724 of the label as well as marking the initials AV in the polar area C5 of areas 711a–711vv of the label.

It should be appreciated that the label of FIG. 7 includes zone and sector markings 750 for ease of use. If desired, a similar label may be placed face up on the bottom of a clear fixitive container for purposes of indexing.

Figure 8:
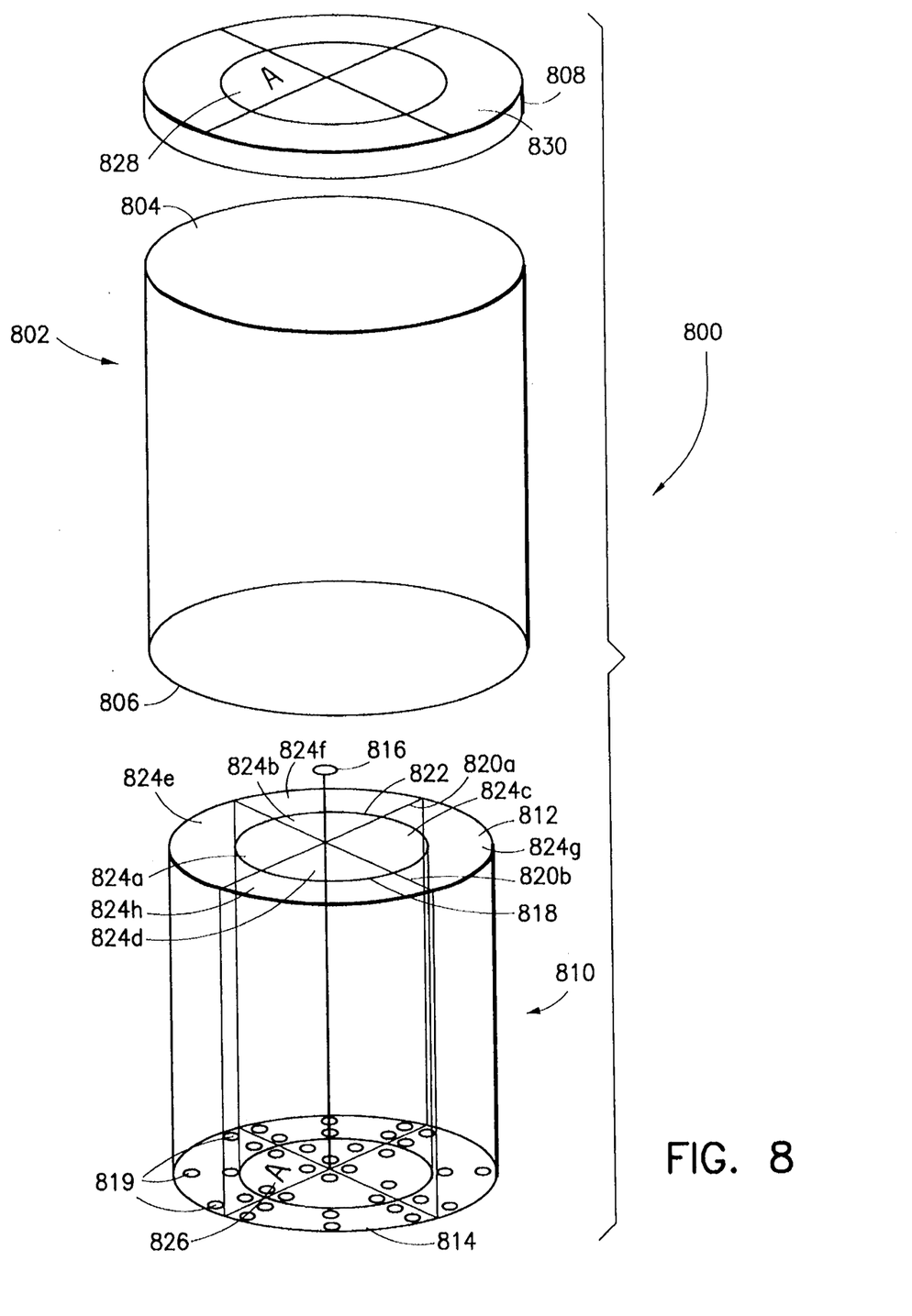
FIG. 8 is a view is a view similar to FIG. 3, but of a fourth embodiment of a multiple sample fixative cup according to the invention.

Turning to FIG. 8, yet another alternative embodiment of the invention is illustrated. A multiple compartment fixative cup 800 includes a cylindrical container 802, with an open top 804 and a closed bottom 806, a removable cover 808 and a removable perforated cylindrical biopsy sample holder 810. The sample holder 810 has an open top 812, a perforated bottom 814, a handle 816 and a partition 818. The partition of the 818 biopsy sample holder 810 is substantially identical to the partition of the multiple compartment fixative cup in FIG. 3 in that it includes a pair of diametrical sector walls 820a and 820b and a cylindrical wall 822 of smaller radius but of substantially equal height to the biopsy sample holder 810. As in FIG. 3, the cylindrical wall 822 is concentrically positioned within the biopsy sample holder 810 and intersects the sector walls 820a and 820b, thereby forming eight "polar" compartments 824a–824h; four radially inner polar compartments, and four radially outer polar compartments. It will be appreciated that in the embodiment of FIG. 8 an aligning index 826 is provided on the sample holder bottom 814 for aligning with an index 828 of the label 830 so that the label areas 830a–830h can be properly matched with the corresponding sample holder compartments 824a–824h. Although the partition 818 of the biopsy sample holder 810 is shown to be identical to the multiple compartment fixative cup as shown in FIG. 3, it will be appreciated that the partitions of the multiple compartment fixative cup illustrated in FIGS. 1 and 5 may also be used.

The height and diameter of the biopsy sample holder 810 are slightly less than that of the container 802, such that it can be contained in the container 802. The perforated bottom 814 of the sample holder contains multiple small holes 819 of sufficient size and number to allow for the rapid draining of a liquid fixative when the biopsy sample holder 810 is removed from the container 802 but not to permit stored biopsy samples from falling out of their compartments. The handle 818 of the biopsy sample holder 810 is axially aligned with the biopsy sample holder 810 and extends from the perforated bottom 814 of the biopsy sample holder 810 to a height greater than that of the biopsy sample holder 810 but less than that of the container 802. This permits the handle 818 to be used to lift the biopsy sample holder 810 in and out of the container 802, yet at the same time to be fully contained within the container 802 when it is closed with the removable cover 808. A thin attachable cover (not shown) can be affixed over the open end of the biopsy sample holder 810 and around the handle to prevent mixing of stored biopsy samples when the biopsy sample holder 810 is contained within the container 802.

The embodiment of FIG. 8 of the invention allows for easy retrieval of biopsy samples stored in the multiple compartment fixative cup 800. The biopsy samples are usually stored in a liquid fixative within the biopsy sample holder 810 which is in turn inside the container 802. Subsequent retrieval of the biopsy samples for analysis is achieved by lifting the biopsy sample holder 810 out of the container 802 by the handle 816 and letting the fixative drain into the container through the perforated bottom 814 of the biopsy sample holder 810. The biopsy samples can then be manually retrieved without the ecumbrance of the fixative.

According to a first method of the invention, the compartments of a fixative container are first prepared with any appropriate biopsy sample fixative. As biopsy samples are being taken with a multiple biopsy instrument, information relating to the biopsy samples is recorded by marking with a noted order the label of the label form in the areas corresponding to the body locations from which the biopsy samples are being taken. When the biopsy samples are removed from the body, the samples are placed in the appropriate corresponding compartments of the container. To find the corresponding compartment, the container index is utilized. The above process is repeated for each group of biopsy samples until there are no more biopsy samples or the fixative container is full. When there are no more biopsy samples or the container is full, the label is removed from the label form and affixed to the removable cover using the index on the cover. The cover is then placed on top of the container with the label index matching the container index such that each area of the label is properly aligned with its corresponding compartment. Alternatively, the cover is placed on top of the container until it is tight, and the the label is then affixed to the cover with the index matching the container index. Regardless, the first record copy containing the same writing as the label is removed from the label form and placed in the chart or file of the patient. The second record copy, also containing the same writing as the label, may be removed from the label form and kept with the closed fixative cup as an extra copy, or may be used as desired for hopsital or other records.

According to a second method of the invention, the compartments of the container of the fixative container are first prepared with any appropriate biopsy sample fixative. As biopsy samples are taken from, e.g., the cervix of a patient, and the surgeon provides information regarding location and a preliminary diagnosis, the appropriate preliminary diagnostic abbreviations are recorded with noted order on the label of the label form in the area corresponding to the location in the patient. If polar coordinate zone information can be recorded, that information is likewise recorded. When the biopsy samples are removed from the patient, they are placed in appropriate container compartments whose location corresponds to the source location on the cervix of the biopsy sample. The above process is repeated until there are no more biopsy samples or the fixative container is full. When there are no more biopsy samples or the container is full, the removable cover may be screwed onto the container and label removed from the label form and affixed in proper alignment, or the label may be removed from the label form and affixed to the removable cover. The cover would then be placed on top of the container with the label index matching the container index 518 such that each area of the label is properly aligned with its corresponding compartment. As with the first method of the invention, the first record copy is then removed from the label form and placed in the chart or file of the patient. The second record copy may be removed from the label form and kept with the closed fixative cup as an extra copy. If available, the polar coordinate information may be attached to the side of the container or another appropriate location. Likewise, the diagnosis abbreviation information is preferably attached to the side of the container.

According to a third method of the invention, if individual biopsies are being obtained, as each biopsy is removed from the body, it is placed in the appropriate location in the container. The corresponding location on the label form is then marked with a preliminary diagnosis initial if desired. Also, if polar coordinates are used, the polar coordinates are also marked. These steps are completed until the cup is full or the biopsy procedure is completed, at which time the label is placed on the cover of the container, and the copy is placed in the records of the patient.

There have been described and illustrated herein several embodiments of an apparatus and method for recording the source and orientation of, as well as for storing and delivering multiple biopsy samples. While particular embodiments of the invention have been described, it is not intended that the invention be limited thereto, as it is intended that the invention be as broad in scope as the art will allow and that the specification be read likewise. Thus, while particular shapes of the fixative container have been disclosed, it will be appreciated that other shapes could be utilized. Also, while various partition means have been shown, it will be recognized that other types of partitions could be used with similar results obtained. Moreover, while particular configurations have been disclosed in reference to the label form, it will be appreciated that other configurations could be used as well. Furthermore, while a preferred embodiment has been disclosed as relating to the coordinates of the cervix, it will be understood that other areas of the body can be similarly related to. Also, while a particular label form and circular labeling set have been disclosed, it will be appreciated that the label form and labeling set can take any of many formats. It will furthermore be understood that, while a particular indexing system has been disclosed it will be understood that any means of properly aligning the labeled cover and the container may be used. It will therefore be appreciated by those skilled in the art that yet other modifications could be made to the provided invention without deviating from its spirit and scope as so claimed.

We claim:

1. An apparatus for recording the source and orientation of, as well as storing and delivering multiple biopsy samples from different sources, comprising:

a) a container with an open top end and a closed bottom end;

b) a cover means for mating with and closing said top end of said container, said cover means having an outer surface;

c) partitioning means within said container forming a plurality of separated non-communicating compartments within said container; and d) labeling means for affixing to said outer surface of said cover means, said labeling means having indicia defining a plurality of areas such that each area corresponds to one of said separated compartments of said container.

2. An apparatus according to claim 1, wherein:

said container is cylindrical in shape and has a radius and a height.

3. An apparatus according to claim 2, wherein:

said partitioning means comprises a plurality of diametrical sector walls, each of said sector walls having a height substantially equal to the height of said container.

4. An apparatus according to claim 3, wherein:

said partitioning means further comprises at least one annular cylinder concentrically disposed within said container and having a smaller radius than that of said container such that upon intersection with said branch wall, radially inner and outer polar zones are formed.

5. An apparatus according to claim 3, wherein:

said partitioning means further comprises a plurality of annular cylinders concentrically disposed within said container, each annular cylinder having a different radius, wherein said radius of said container is greater than said radii of said annular cylinders, wherein intersections between said annular cylinders and said branch walls form at least radially inner, middle, and outer polar zones.

6. An apparatus according to claim 4, wherein:

said compartments are correlated to locations on a cervix for collection of multiple cervical biopsy samples.

7. An apparatus according to claim 2, wherein:

said partitioning means further comprises at least one annular cylinder concentrically disposed within said container and having a smaller radius than that of said container.

8. An apparatus according to claim 2, wherein:

said partitioning means further comprises a plurality of annular cylinders concentrically disposed within said container, each annular cylinder having a different radius smaller than said radius of said container.

9. An apparatus according to claim 8, wherein:

said compartments are correlated to locations on a cervix for collection of multiple cervical biopsy samples.

10. An apparatus according to claim 1, wherein:

said labeling means includes at least a top first layer and a second layer with pressure sensitive means for causing a copy of writing on said top first layer to appear on said second layer, said top first layer having adhesive means for affixing said top first layer to said cover means.

11. An apparatus according to claim 10, wherein:

said container has a first indicator means for locating a first compartment of said container, and said labeling means has a second indicator means for aligning said labeling means on said cover.

12. A method for recording the source and orientation of, as well as for storing multiple biopsy samples in a fixative container having a plurality of compartments, wherein the fixative container is provided with a cover and is further provided with a label set having a top first layer, a second layer, and pressure sensitive means for causing a copy of writing on the top first layer to appear on the second layer, the label set having first indicia defining areas corresponding to the plurality of compartments of the container, where the label can be affixed to the cover, said method comprising the steps of:

a) taking multiple biopsy samples from a plurality of locations in a patient;

b) marking the top first layer of the label set in areas corresponding to the plurality of locations;

c) placing each biopsy sample in a separate compartment of the fixative container;

d) covering the fixative container with the cover;

e) affixing at least one of the top first layer and the second layer of the label set to the cover; and f) locating the other of the top first layer and the second layer of the label set in a chart or file of the patient.

13. A method according to claim 12, wherein:

the multiple biopsy samples are taken from a plurality of locations in the cervix of the patient.

14. A method according to claim 12, wherein:

a plurality of said multiple biopsy samples are taken with a multiple biopsy sample tool, and said said step of marking includes indicating an order in which the samples are taken.

15. A method according to claim 12, wherein:

said marking step includes providing a preliminary diagnosis indication.

16. A method according to claim 15, wherein:

said label set includes a portion indicating diagnoses and abbreviations of diagnoses, said preliminary diagnosis indication comprises at least one of said abbreviations, and said method further comprises attaching the portion of the label set indicating diagnoses and abbreviations of diagnoses to the container.

17. A method according to claim 12, wherein:

the container has a first indicator for locating a first compartment of the container, the label set has a second indicator indicating an area of the label set corresponding to the first compartment, and said method further comprises aligning said label on said cover such that when said cover covers said container, said second indicator substantially aligns with said first indicator.

18. A method according to claim 12, wherein:

the label set includes a portion indicating polar coordinate information regarding one of polar zone and sector, and said method further comprises marking said label set at said portion indicating polar coordinate information with the other of polar zone and sector to complete the polar coordinate information.

19. An apparatus according to claim 1, further comprising:

c) a biopsy sample holder, wherein, said container has a first height and a first diameter;

said biopsy sample holder has a second height and a second diameter, said second height being smaller than said first height and said second diameter being smaller than said first diameter, said biopsy sample holder including said partitioning means and said biopsy sample holder further having, an open top, a substantially closed bottom having a plurality of perforations, said perforations being large enough to allow for the drainage of a fixative and small enough to prevent the loss of stored biopsy samples, and a handle extending along a central axis of said biopsy sample holder, said handle extending above said partitioning means, but fitting within said container when said top of said container is closed by said cover means.

20. An apparatus according to claim 19, wherein:

said partitioning means comprises a plurality of diametrical sector walls, each of said sector walls having a height substantially equal to said second height.

21. An apparatus according to claim 20, wherein:

said partitioning means further comprises at least one annular cylinder concentrically disposed within said biopsy sample holder and having a smaller diameter than said second diameter.

22. An apparatus according to claim 19, wherein:

said labeling means includes at least a top first layer and a second layer with pressure sensitive means for causing a copy of writing on said top first layer to appear on said second layer, said top first layer having adhesive means for affixing said top first layer to said cover means.

23. An apparatus according to claim 19, wherein:

said biopsy sample holder has a first indicator means for locating a first compartment of said biopsy sample holder, and said labeling means has a second indicator means for aligning said labeling means on said cover.

* * * * *